(12) United States Patent
Sarradon

(10) Patent No.: US 8,858,514 B2
(45) Date of Patent: Oct. 14, 2014

(54) INTERNAL DEVICE FOR INJECTION AND SAMPLING OF A LIQUID INSIDE A LIVING ORGANISM

(76) Inventor: Pierre Sarradon, Toulon (FR)

( * ) Notice: Subject to any disclaimer, the term of this patent is extended or adjusted under 35 U.S.C. 154(b) by 345 days.

(21) Appl. No.: 13/159,987

(22) Filed: Jun. 14, 2011

(65) Prior Publication Data

US 2012/0323225 A1    Dec. 20, 2012

(51) Int. Cl.

| A61M 37/00 | (2006.01) |
|---|---|
| A61B 5/155 | (2006.01) |
| A61M 39/02 | (2006.01) |
| A61M 1/36 | (2006.01) |
| A61B 5/15 | (2006.01) |
| A61M 25/00 | (2006.01) |
| A61B 5/153 | (2006.01) |

(52) U.S. Cl.
CPC .............. *A61B 5/1427* (2013.01); *A61B 5/155* (2013.01); *A61M 39/0208* (2013.01); *A61M 1/3653* (2013.01); *A61M 2039/022* (2013.01); *A61M 25/0052* (2013.01); *A61B 5/15003* (2013.01); *A61B 5/153* (2013.01)
USPC ................................ 604/288.02; 604/288.04

(58) Field of Classification Search
USPC .................................. 604/27, 288.01–288.04
See application file for complete search history.

(56) References Cited

U.S. PATENT DOCUMENTS

| 4,184,497 | A | 1/1980 | Kolff et al. | |
|---|---|---|---|---|
| 6,595,941 | B1 * | 7/2003 | Blatter | 604/4.01 |
| 7,101,356 | B2 * | 9/2006 | Miller | 604/288.02 |
| 7,118,546 | B2 * | 10/2006 | Blatter | 604/6.16 |
| 8,088,112 | B2 * | 1/2012 | Chantriaux et al. | 604/288.02 |
| 2007/0083156 | A1 | 4/2007 | Muto et al. | |
| 2007/0088336 | A1 | 4/2007 | Dalton | |

FOREIGN PATENT DOCUMENTS

DE    39 27 001 A1    2/1991

* cited by examiner

*Primary Examiner* — Emily Schmidt
(74) *Attorney, Agent, or Firm* — Frommer Lawrence & Haug LLP; Ronald R Santucci

(57) ABSTRACT

The invention concerns a device to inject and/or to take a sample, with the aid of a needle, of a liquid inside the organism of a living being, through the skin in a repeated manner.

More particularly, the present invention concerns a device intended to be implanted inside a living, human or animal organism, presenting a vascular system and a skin, to exchange a liquid with the vascular system, through the skin and in a repeated manner, using a needle, the aforementioned device including at least a first tubular puncture site, shaped to be able to be perforated numerous times over all its length, the tubular puncture site being linked up in a watertight manner with a flexible link conduit with the vascular system, the tubular puncture site including an watertight flexible tubing, supported by reinforcement constituted by rigid rings, this being shaped to allow the puncture site to lose its shape to follow the body movements of the patient without causing discomfort.

The present invention also concerns a system of dialysis including such a device.

10 Claims, 3 Drawing Sheets

INTERNAL DEVICE FOR INJECTION AND SAMPLING OF A LIQUID INSIDE A LIVING ORGANISM

TECHNICAL FIELD OF THE INVENTION

The present invention concerns the field of devices to inject and/or to take a sample, with the aid of a needle, of a liquid inside one of the organs of a living being, through the skin in a repeated fashion.

STATE OF THE PRIOR ART

A catheter is composed of a small conduit, fine and sterile, intended to be implanted in a vein in order to be able to inject or take a sample of products in the blood system of a patient. A catheter enables repeated injections into the body of the patient to be avoided, what can become difficult to bear in the case of long-term medical treatments. A catheter is linked in general to an injection site, intended to be pierced.

This injection site is generally located on the outside of the body of the patient, as illustrated in document FR 2 471 195. However, in the case of long-term treatments, this injection site, outside the body but in contact with the blood system of the patient, can be a source of infections, especially in the case of long-term treatments such as chemotherapy or dialysis.

Entirely internal catheter devices, or implantable injection sites, have therefore been developed: it is for example the case of the device described in the document U.S. Pat. No. 5,922,104. This implantable injection catheter site has a small sterile reservoir which is put under the skin and is connected to a conduit inserted, most often, in the sub-clavicle or jugular vein. A small incision from 3 to 4 cm is necessary, and some stitches then hold the system in place. This type of catheter is favourable because, contrary to precedent, it does not require particular hygiene care and risks of infection are limited. However, further to the implementation of such a device, punctures always take place in the same place, that is to say above the reservoir, which leads to very many coetaneous perforations on a reduced zone, so the risk of infection or coetaneous necroses is high.

Moreover, documents EP0699424 and EP1148843 describe implantable tubular prosthesis in PTFE, reinforced by an external helicoidal support as well as the manufacturing techniques of such a prosthesis.

In the document US 2007/0083156 is described an injection or puncture site allowing successive closely spaced punctures away from a puncture zone, to avoid the multiplication of punctures in the same place and the allied risks of infection. The device is rigid, in the sense that it does not allow the flexibility required to follow the movements of the patient. Indeed, the offered puncture site is constituted of a tubular body in thick elastomer, reinforced if necessary by a rigid support element. The tubular body is constituted by an elastomer sleeve folded back on itself, so as to introduce an increasing density from the outside to the inside of the body, or alternately by a pair of coaxial sleeves, the internal sleeve having a greater external diameter than the internal diameter of the internal sleeve. The objective here is to get a density of elastomer that increases from the outside to the inside of the tubular body, so that the material closes again hermetically on itself after puncture by a needle. The rigid element can be made up of a spiral compression spring or by a rigid stent. The puncture site is therefore constituted of a rather rigid tubular body reinforced by a support element which is itself rigid. If limited deformations due to flexing are possible, they will be due to elastic distortions of the tubular body and of the rigid support. The patient, assuming that by their own movements they manage to bend the puncture site, will nevertheless feel the mechanical solicitations of the site, attempting to return to its initial form, which will be particularly uncomfortable.

DISCLOSURE OF THE INVENTION

The present invention aims at overcoming the disadvantages of the state of technology by offering a device, an implantable puncture site, allowing punctures to be made using a needle through the skin at numerous points divided successively on an extensive surface to allow the skin to heal in the previous puncture points. For this, the device according to the present invention is composed of a fine and sterile conduit intended to be established in a conduit of the vascular system, vein, artery or prosthesis, linked up in an airtight way with a tubular puncture site, intended to be inserted under the skin, which is long enough and that can be punctured on all its length. In a remarkable manner, this puncture site is flexible, to follow the body movements of the patient without incommoding it, in spite of its length, while being resistant enough to resist numerous punctures.

The selected tubular puncture site is therefore constituted of a watertight micro porous membrane, for example in expanded PTFE, like Gore-tex®. Such a membrane is biocompatible and can be punctured numerous times, while keeping its watertight quality. Moreover, to give the mechanical resistance necessary for the puncture site, without reducing its flexibility, this membrane is reinforced by a shell, also in biocompatible material, and which forms individual rings around the cavity of the puncture site. This shell avoids the tubular puncture site being crushed during punctures, but does not reduce its flexibility.

More particularly, the present invention concerns a device intended to be implanted inside a living, human or animal organism, with a vascular system and a skin, to exchange, through the skin and in a repeated way, with the aid of a needle, a liquid with the vascular system, the said device including at least a first tubular puncture site, shaped to be able to be perforated numerous times over all its length, the tubular puncture site being linked up in an watertight way with a flexible link conduit with the vascular system, the tubular puncture site being linked to a watertight flexible tube, supported by a reinforcement of rigid rings, the reinforcement being shaped to allow the puncture site to lose its shape longitudinally while having a transverse rigidity allowing the puncture.

The reinforcement by rigid rings allows the puncture site on one hand to be rigid transversely, to allow punctures without crushing the site, and on the other hand to be flexible longitudinally, to allow the puncture site to follow the body movements of the patient.

The flexible tube can be punctured over all its length, between the rigid rings, which allows to the practitioner to change puncture site between two successive punctures. This tubing remains watertight in spite of the different punctures thanks to tissue from the human body which stops the hole in the puncture site after every puncture.

The tubular puncture site can include a flexible cylinder, similar, for example to those described in documents EP1148843 or EP0699424, including one shell and one or two layers of expanded PTFE. The use of reinforcement made up of rigid rings is favourable because it enables the puncture site to be flexible and on the whole deformable so as to follow the body movements of the patient and therefore improve comfort, while being resistant to the numerous punctures. Indeed, the rigid ring reinforcement avoids the puncture site being crushed under the pressure of punctures. Furthermore, the puncture site can be punctured over all its length, since during a puncture, the needle slips between two rings of the reinforcement. In this way the reinforcement allows the puncture site to maintain its tubular form in spite of the different punctures, without therefore hindering successive punctures, and over all the length of the puncture site.

The reinforcement can be in metal or in polymer.

Favourably, the flexible tubing is made of micro porous material, preferably expanded PTFE. Indeed, expanded PTFE is biocompatible, it resists the repeated punctures well and has exceptional waterproof qualities.

In other words, invention enables a considerable augmentation of the length of the puncture site without additional discomfort for the patient, the flexibility of the site allowing it to adapt to body movements.

In a particular mode of realisation of the present invention, the flexible tubing forms a smooth wall delimiting a tubular cavity of the puncture site and separating the reinforcement from the cavity. Thus, the internal wall of the puncture site, which is in contact with the blood, is smooth, which avoids the formation of clots in the puncture site.

In a favourable way, the reinforcement can be included between two watertight membranes, which prevents harm to the skin under which the puncture site is inserted, by having a wall just as smooth as the outside of the puncture site.

The puncture site can have a length between 4 and 15 cm, a length which is sufficient to give numerous puncture zones and so enabling the skin to heal between two punctures, and which is not excessive to avoid bothering the patient. Furthermore, in this way, the incision to be made to set up the device remains relatively restricted.

The puncture site can have an internal diameter included between 5 and 10 mm, preferred between 5.5 and 6.5 mm. This diameter should be small so that the puncture site is not too bulky for the patient who carries it, but be broad enough so that during puncture, the needle does not cross straight through the puncture site. Indeed, if the puncture site is too slim, it will be difficult for the nurse making the puncture to dose the depth to insert the needle to attain the internal cavity of the puncture site.

According to a preferred method, the tubular puncture site is closed at the end of the flexible link conduit, so as to form a simple bag.

For bypass application, it will, on the contrary, be possible to open the end of the puncture site opposite to the flexible link conduit.

The invention also concerns a system which includes two devices as previously described, the tubular puncture sites of both devices preferably being united in a common scabbard, but separated by a watertight wall, and the puncture sites being tied together, to avoid both devices separating in the human body. One of the devices is used to take blood samples from the organism, of the other one to inject the reprocessed blood or the blood substitution liquid.

BRIEF DESCRIPTION OF THE DRAWINGS

Other characteristics and advantages of the invention will become evident in reading the following description, with reference to the related figures, which illustrate.

For increased clarity, identical or similar elements are marked with identical reference signs on all the of the figures.

DETAILED DESCRIPTION OF THE USAGE METHOD

Figure 1:
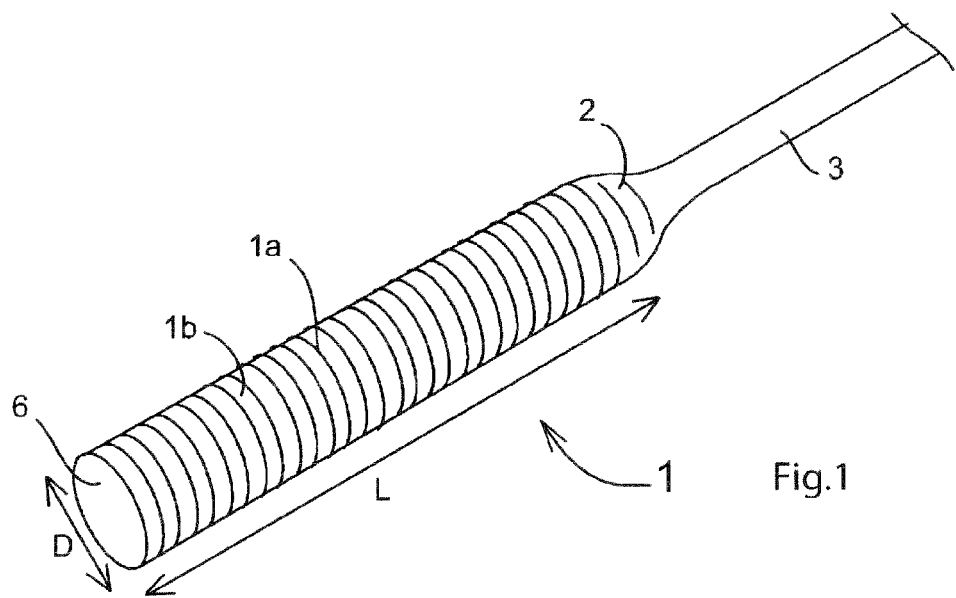
FIG. 1, a schematic representation of a device according to the present invention.

In reference to FIG. 1, a device correspondent to the present invention, intended for dialysis, includes a tubular puncture site 1, blocked by a hermetic wall in an axial end 6 and linked up by its axial end to a silicone flexible conduit 3 using a watertight connection 2. The tubular puncture site 1 includes a micro porous tissue 1b supported by annular reinforcements 1a. Such tubes are known to previous art and are more amply described, as well as their manufacturing technique, in the document EP0699424. The tubular puncture site so constituted is flexible but resists the different punctures and does not crush during penetration by a needle. Moreover, in spite of repeating punctures, it is watertight. Other flexible cylinders can be used as puncture site, for example those described in the document EP1148843, which describes a flexible cylinder including the first and second layer of expanded polytetrafluoroethylene and a dilatable support layer, at least one of the layers of polytetrafluoroethylene containing a multiplicity of spaced out openings. This type of cylinder introduces the advantage of being particularly flexible. Moreover, the support is included between two layers of polytetrafluoroethylene, which allows the formation of blood clots in the tubular puncture site, and avoids hurting the skin outside the tubular puncture site. These documents should be referred to for more precision on the composition of these flexible cylinders.

In this example, where the device is used to accomplish a dialysis, the tubular puncture site has a 6 mm diameter and a 10 cm length. The length of the tubular puncture site depends on the punctures which will be performed in the puncture site: the greater the number and frequency of punctures, the greater the surface of the tubular puncture site, to allow the skin to heal between two punctures. The conduit 3 has here a 2 mm diameter. The diameters of the conduit 3 and of the puncture 1 site depend on the application of the device: the greater the debit of blood to be taken, the greater will be the diameters. Typically, in the case of a dialysis, as it is case here, diameters will be greater than in the case of a chemotherapy, since the volumes of exchanged liquids are more important in the case of dialysis than in the case of a chemotherapy.

Figure 2:
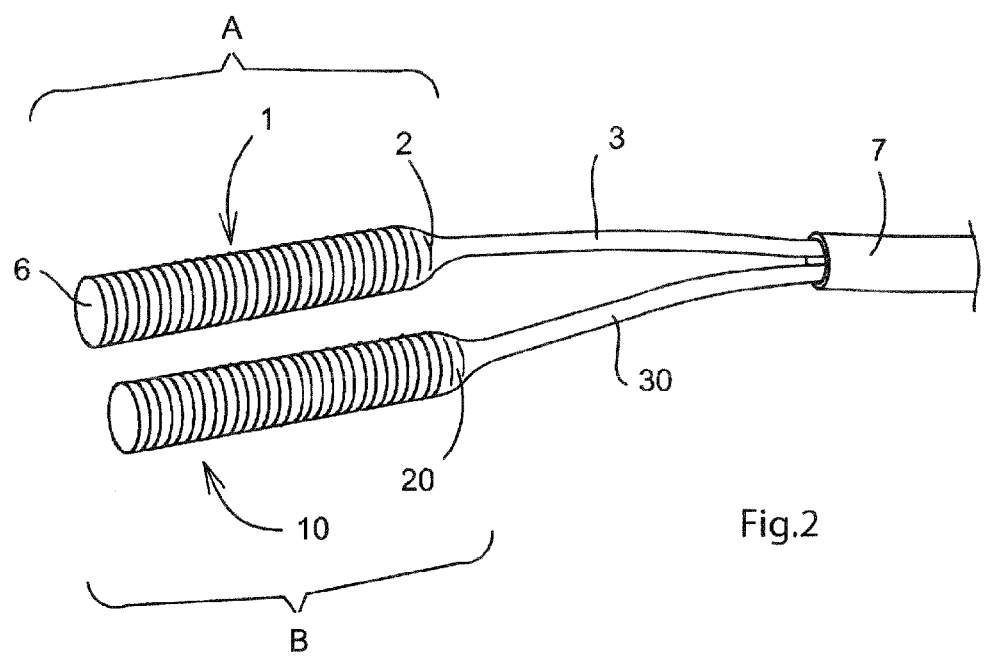
FIG. 2, a schematic representation of a system according to the present invention enabling the injection of one liquid and sampling of another one.

FIG. 2 represents another method of use according to the present invention in which the device described hereinbefore is constituted of the tubular puncture site 1 linking up by a watertight connection in the conduit 3 is linked to a similar device constituted also of a tubular puncture site 10 linked up by a watertight connection 20 with a conduit 30. Pipes 3, 30 of these two devices A and B are gathered in a scabbard 7 which avoids that pipes 3, 30 separating in the human body.

Figure 3:
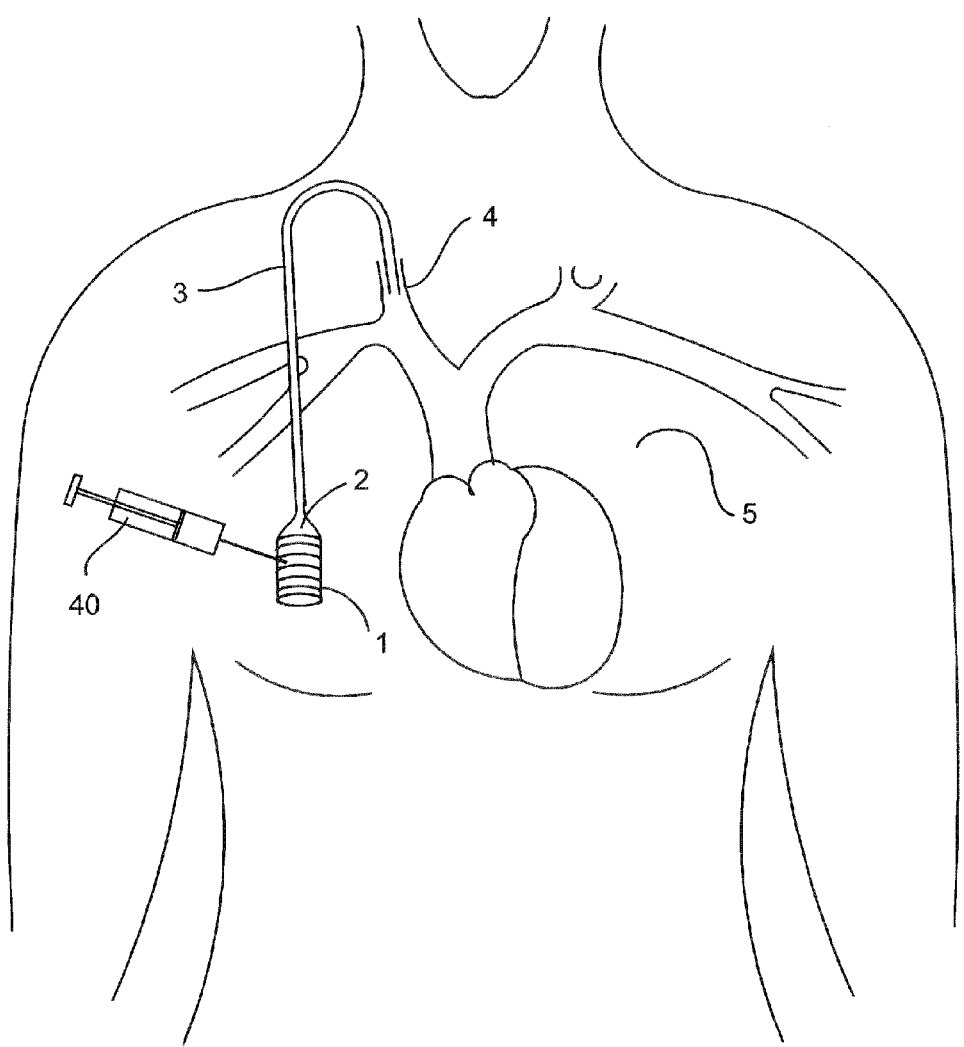
FIG. 3, a schematic representation of positioning in the human body of a device according to the present invention.

FIG. 3 gives a diagram of the location of the device in FIG. 1. The tubular puncture site 1 is put in the skin of the torso 5 of the patient while the conduit 3 is linked to the artery 4 of the patient.

Figure 4:
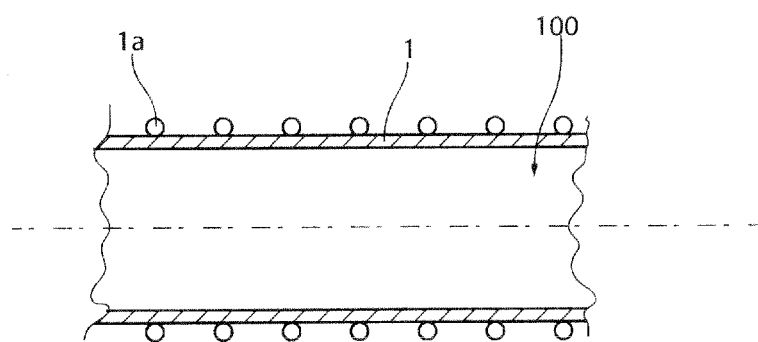
FIG. 4, a schematic representation of a section of a device according to one embodiment of the invention.

In the embodiment illustrated in FIG. 4, the flexible tubing 1 forms a smooth wall delimiting a tubular cavity 100 of the puncture site and separating the reinforcement 1a from the cavity 100. Thus, the internal wall of the puncture site, which is in contact with the blood, is smooth, which avoids the formation of clots in the puncture site.

Figure 5:
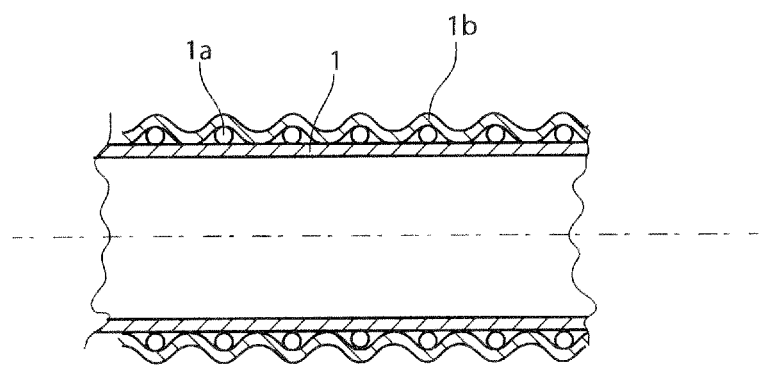
FIG. 5, a schematic representation of a section of a device according to another embodiment of the invention.

In the embodiment illustrated in FIG. 5, the reinforcement 1a can be included between two watertight membranes 1 and 1b, which prevents harm to the skin under which the puncture site is inserted, by having a wall just as smooth as the outside of the puncture site.

Such a device can arranged in this way in the case of treatments such as dialysis or chemotherapy. To put this device into the body of the patient, a small incision from 2 to 4 cm is made in the torso 5 of the patient under local anaesthesia, then the conduit 3 is slipped into the jugular vein 4. After this, a few stitches close the incision and support the device in place. Tube 1 is thus placed permanently under the skin of the patient, which avoids it going septic. To inject or to take a sample of a liquid in the blood system of the patient, this tube 1 is punctured across the skin, with the aid of a needle 40.

This device does not require particular hygiene care and the patient can therefore live normally between two punctures, without caring about the implant. Indeed, the comfort of the patient is favoured by the suppleness of the puncture site, which follows the movements of the torso thereby minimising discomfort for the patient. Moreover, given the extent of the surface of available puncture site on the tubular puncture, successive punctures can be progressively brought forward to let the skin heal.

At the end of treatment, this device can be withdrawn under local anaesthesia.

Naturally, many variants are possible: for example, more than two tubular injection sites can be united in a device similar to that on FIG. 2. Moreover, the flexible tubing can be constituted of other biocompatible and watertight material. It is also possible to create the conduit in any other flexible, biocompatible and watertight material. Moreover, the dimensions of the device depend on intended application, and also on type of patient for which the device is intended: the diameter of the puncture site and of the conduit will be greater in the case of dialysis than in the case of chemotherapy, and it will be possible to envisage several sizes of devices according to the size of blood vessels used. The device can moreover be used in animals.

According to a variant, the tubular puncture site 1 can be devoid of bottom blocking axial end 6, so as to form with the flexible silicone 3 tube a conduit coming out with two free ends. The device constituted in this way is particularly adapted to a bypass shape, notably between an artery and a vein. End 6 is then shunted in an artery, for example the humeral artery, while the flexible silicone 3 conduit is inserted in a vein, for example a humeral vein, to a depth of at least 2-4 cm, and shunted in the vein. During the establishment of the bypass, care is taken to leave at least a part of the tubular puncture site 1 close to the skin, and this on a sufficient length to allow injections or punctures using a needle through the skin.

The invention claimed is:

1. A device intended to be implanted inside a living, mammalian organism, presenting a vascular system and skin, to exchange a liquid with the vascular system through the skin and in a repeated manner using a needle, the device including at least a first tubular puncture site including:

a watertight flexible bendable tubing, having a length of between 4 cm and 15 cm and being shaped to be perforated numerous times over all said length, the flexible bendable tubing being supported by a reinforcement consisting of rigid individual rings to allow the puncture site to change shape to follow the body movements of the organism without causing discomfort, the flexible bendable tubing being linked up to the vascular system in a sealed manner with a flexible link conduit, the flexible link conduit having an external diameter smaller than an external diameter of the flexible tubing, the diameter of the flexible link conduit and a length of the flexible link conduit being such that the flexible link conduit is insertable into a vessel of the vascular system over a depth of at least 2 to 4 cm, and the flexible link conduit being without reinforcement.

2. The device of claim 1, wherein the reinforcement is made of a polymer or a metal.

3. The device of claim 1, wherein the flexible bendable tubing includes a micro porous material.

4. The device of claim 1, wherein the flexible bendable tubing forms a smooth wall delimiting a tubular cavity on the tubular puncture site and separating the reinforcement from the cavity.

5. The device of claim 1, wherein the reinforcement is included between two watertight membranes.

6. The device of claim 1, wherein the tubular puncture site is closed at the end opposite to the flexible link conduit.

7. The device of claim 1, wherein the tubular puncture site is opened at its end opposite to the flexible link conduit.

8. A blood dialysis system, characterised by the fact that it includes two devices according to claim 1.

9. The blood dialysis system of claim 8, wherein the tubular puncture sites are linked together.

10. A device intended to be implanted inside a living, mammalian organism, presenting a vascular system and a skin, to exchange a liquid with the vascular system through the skin and in a repeated manner using a needle, including at least:

a sterile flexible bendable conduit linked up in a sealed manner with a tubular puncture site intended to be put under the skin, the puncture site being flexible and bendable to follow the body movements of the patient without causing discomfort, and constituted by a watertight biocompatible micro porous membrane, capable of being punctured numerous times while retaining waterproof qualities, the membrane delimiting a tubular puncture cavity having a length of between 4 cm and 15 cm and being reinforced by individual rings made of biocompatible material extending around the tubular puncture cavity, the sterile flexible bendable conduit having an external diameter smaller than an external diameter of the flexible bendable tubular puncture site, the diameter of the flexible bendable conduit and a length of tile flexible bendable conduit being such that the flexible bendable conduit is insertable into a vessel of the vascular system over a depth of at least 2 to 4 cm, and the flexible bendable conduit bring without reinforcement.

* * * * *